(12) United States Patent
Auvray et al.

(10) Patent No.: US 10,918,359 B2
(45) Date of Patent: Feb. 16, 2021

(54) ULTRASOUND IMAGING ASSEMBLY AND METHOD FOR DISPLAYING ULTRASOUND IMAGES

(71) Applicant: KONINKLIJKE PHILIPS N.V., Eindhoven (NL)

(72) Inventors: Vincent Maurice André Auvray, Meudon (FR); Remi Nicolas Thierry Cuingnet, Colombes (FR); Roberto José Ardon, Sèvres (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1066 days.

(21) Appl. No.: 15/105,234

(22) PCT Filed: Dec. 15, 2014

(86) PCT No.: PCT/EP2014/077775
§ 371 (c)(1),
(2) Date: Jun. 16, 2016

(87) PCT Pub. No.: WO2015/091368
PCT Pub. Date: Jun. 25, 2015

(65) Prior Publication Data
US 2016/0317130 A1    Nov. 3, 2016

(30) Foreign Application Priority Data

Dec. 20, 2013  (EP) .................................... 13306807

(51) Int. Cl.
*A61B 8/08*       (2006.01)
*G06T 7/00*       (2017.01)
(Continued)

(52) U.S. Cl.
CPC .......... *A61B 8/5269* (2013.01); *A61B 8/4483* (2013.01); *A61B 8/461* (2013.01);
(Continued)

(58) Field of Classification Search
CPC ........... A61B 8/00; A61B 8/08; A61B 8/5269; A61B 8/4483; A61B 8/461; A61B 8/467;
(Continued)

(56) References Cited

U.S. PATENT DOCUMENTS 9,471,981 B2    10/2016  Arai et al.
2003/0125621 A1  7/2003  Drukker et al.
(Continued)

FOREIGN PATENT DOCUMENTS

EP         2272434 A1    1/2011
JP         2003325514   11/2003
(Continued)

OTHER PUBLICATIONS

Machine translation of Shigemori et al. (JPO Pub. JP 2003325514 A, Nov. 18, 2003).*
(Continued)

*Primary Examiner* — Carolyn A Pehlke (57) ABSTRACT

An ultrasound imaging assembly is disclosed, comprising an image processing unit (26) for receiving and for evaluating at least one set of ultrasound data resulting from an ultrasound scan of a volume of interest (31) and for providing corresponding image data on the basis of the ultrasound data. The assembly comprises a display unit (18) for displaying an ultrasound image (30) on the basis of the image data, and an evaluation unit (28) adapted to detect whether a shadowed area (32) is present within the volume of interest (31) on the basis of the ultrasound data, wherein the image processing unit is adapted to determine ultrasound image data of a two-dimensional slice of the shadowed area and wherein the display unit is adapted to display a graphical representation of a corresponding sectional view of the shadowed area within the ultrasound image.

18 Claims, 5 Drawing Sheets

(51) Int. Cl.
*G06T 7/11* (2017.01)
*G06T 7/62* (2017.01)
*A61B 8/00* (2006.01)

(52) U.S. Cl.
CPC .............. *A61B 8/467* (2013.01); *A61B 8/483* (2013.01); *A61B 8/5215* (2013.01); *A61B 8/54* (2013.01); *G06T 7/0012* (2013.01); *G06T 7/11* (2017.01); *G06T 7/62* (2017.01); *A61B 8/085* (2013.01); *A61B 8/466* (2013.01); *G06T 2207/10132* (2013.01)

(58) Field of Classification Search
CPC ......... A61B 8/483; A61B 8/52; A61B 8/5215; A61B 8/523; A61B 8/5238; A61B 8/54; A61B 8/085; A61B 8/466; G06T 7/62; G06T 7/11; G06T 7/0012
See application file for complete search history.

(56) References Cited

U.S. PATENT DOCUMENTS

| | | | |
|---|---|---|---|
| 2003/0161513 A1 | 8/2003 | Drukker et al. | |
| 2005/0113695 A1 | 5/2005 | Miller | |
| 2009/0062644 A1* | 3/2009 | McMorrow | A61B 8/08 600/437 |
| 2010/0036242 A1* | 2/2010 | Yuk | A61B 5/02014 600/437 |
| 2012/0243757 A1 | 9/2012 | Funka-Lea et al. | |
| 2013/0197357 A1* | 8/2013 | Green | A61B 8/0841 600/424 |
| 2014/0187947 A1* | 7/2014 | Hansegard | A61B 8/52 600/440 |
| 2014/0307920 A1* | 10/2014 | Holz | G06K 9/00335 382/103 |
| 2015/0002538 A1* | 1/2015 | Sohn | A61B 8/5223 345/629 |

FOREIGN PATENT DOCUMENTS

| | | |
|---|---|---|
| JP | 2003325514 A | 11/2003 |
| JP | 2010207492 A | 9/2010 |
| JP | 2013192673 A | 9/2013 |
| WO | 2010017508 A1 | 2/2010 |

OTHER PUBLICATIONS

Hellier et al "Acoustic Shadows Detection, Application to Accurate Reconstruction of 3D Intraoperative Ultrasound" IEEE International Symposium on Biomedical Imaging: From Nano to Macro, May 2008 Paris, France.

Hellier, et al., "An automatic geometrical and statistical method to detect acoustic shadows in intraoperative ultrasound brain images", Medical Image Analysis 14, 2 (2010), 195-204 (Abstract).

Karamalis, et al., "Ultrasound confidence maps using random walks", Medical Image Analysis, Aug. 2012, 16(6), 1101-1112 (Abstract).

* cited by examiner

ULTRASOUND IMAGING ASSEMBLY AND METHOD FOR DISPLAYING ULTRASOUND IMAGES

This application is the U.S. National Phase application under 35 U.S.C. § 371 of International Application No. PCT/EP2014/077775, filed on Dec. 15, 2014, which claims the benefit of European Patent Application No. 13306807.2, filed Dec. 20, 2013. These applications are hereby incorporated by reference herein.

FIELD OF THE INVENTION

The present invention relates to an ultrasound imaging assembly for ultrasound imaging. The present invention further relates to a method for displaying ultrasound images. Finally, the present invention relates to an ultrasound transducer assembly including ultrasound transducer elements for transmitting and receiving ultrasound waves.

BACKGROUND OF THE INVENTION

In the field of ultrasound imaging, it is generally known that the ultrasound images are subjected to different artifacts, which have to be distinguished from anatomic objects in the volume of interest in order to provide a reliable medical examination of a patient. One of the most important artifacts are the acoustic shadows. The ultrasound images are based on the propagation and interaction of ultrasound waves in tissues and anatomic objects of various acoustic impedances. At the boundaries of two materials having different impedances, the ultrasound waves are transmitted, reflected, dispersed or diffracted. If the acoustic energy is almost totally reflected or dispersed, an acoustic shadow appears in an area of the volume of interest beyond the respective boundary. These shadowed areas may cause major issues, since these shadowed areas are totally obscured in the respective ultrasound image and may hide an area of interest.

Due to the different anatomic properties, some organs or regions of the human body are difficult to analyze without introducing acoustic shadows because the ultrasound probe has to be positioned at the thorax so that the acoustic waves are reflected or dispersed at the ribs and the areas beyond are obscured by the resulting acoustic shadow.

In the field of ultrasound imaging, it is known to detect acoustic shadows within the ultrasound image automatically and to correct the shadowed areas within the ultrasound image for example by overlaying different ultrasound images. It is further known from US 2012/0243757 A1 to detect the shadowed areas and to display merely those ultrasound images which show a reduced amount of shadowed areas.

Hence, the known ultrasound imaging systems do not distinguish shadowed areas from anatomic objects, however the operator has to make sure that the shadowed areas do not obscure a region of interest, which is important for the medical examination.

SUMMARY OF THE INVENTION

It is an object of the present invention to provide an improved ultrasound imaging assembly, in particular for 3D ultrasound imaging, having improved imaging conditions so that a more reliable examination is possible. It is further an object of the present invention to provide a corresponding method for ultrasound imaging.

In a first aspect of the present invention, an ultrasound imaging assembly is provided comprising:
an image processing unit for receiving and for evaluating at least one set of ultrasound data resulting from an ultrasound scan of a volume of interest and for providing corresponding image data on the basis of the ultrasound data,
a display unit for displaying an ultrasound image on the basis of the image data,
an evaluation unit adapted to detect whether a shadowed area is present within the volume of interest on the basis of the ultrasound data,
wherein the image processing unit is adapted to determine ultrasound image data of a two-dimensional slice of the shadowed area and wherein the display unit is adapted to display a graphical representation of a corresponding sectional view of the shadowed area within the ultrasound image.

In a further aspect of the present invention, a method for displaying ultrasound images is provided comprising the steps of:
receiving at least one set of ultrasound data resulting from an ultrasound scan of a volume of interest,
evaluating the at least one set of ultrasound data,
providing corresponding image data on the basis of the ultrasound data,
displaying an ultrasound image on a display unit on the basis of the image data,
detecting whether a shadowed area is present within the volume of interest on the basis of the ultrasound data, and
determining ultrasound image data of a two-dimensional slice of the shadowed area and displaying a graphical representation of a corresponding sectional view of the shadowed area within the ultrasound image on the display unit.

In a still further aspect of the present invention, an ultrasound transducer assembly is provided comprising an ultrasound transducer unit including the plurality of ultrasound transducer elements for transmitting and receiving ultrasound waves and an ultrasound imaging assembly of this kind for evaluating and displaying ultrasound data received from the ultrasound transducer unit.

Preferred embodiments of the invention are defined in the dependent claims. It should be understood that the claimed method has similar and/or identical preferred embodiments as the claimed device and as defined in the dependent claims.

The present invention is based on the idea to determine whether a shadowed area or a plurality of shadowed areas are present within the volume of interest by evaluating the ultrasound data and to indicate on the display unit whether a shadowed area has been detected within the volume of interest and to determine image data of a two-dimensional slice of the shadowed area and to display a corresponding sectional view of the shadowed area in order to indicate that certain regions of interest are obscured and where the obscured areas are located. The operator can consider the ultrasound data and can verify whether the region of interest is obscured or a high quality ultrasound image is provided. Hence, the operator is able to ensure that the region of interest is analyzed with an optimal quality and no acoustic shadows obscure the region of interest so that the overall reliability of the medical examination is increased.

In a preferred embodiment, the display unit is further adapted to indicate whether no shadowed area has been detected within the volume of interest. This is a possibility to indicate to the operator that high quality images are displayed and no area is obscured.

In a preferred embodiment, the display unit is adapted to indicate whether a shadowed area has been detected within the volume of interest.

In a preferred embodiment, a warning message is displayed on the display unit. This is a simple possibility to indicate that a shadowed area has been detected.

In a preferred embodiment, the evaluation unit is adapted to detect a position of the shadowed area within the volume of interest and the display unit is adapted to display a graphical representation of the shadowed area within an ultrasound image. This is a possibility to reduce the duration of the analysis, since the position of the shadowed area is displayed so that the operator can easily decide whether a detailed analysis is necessary.

In a preferred embodiment, the evaluation unit is adapted to determine a size of the detected shadowed area and the display unit is adapted to display a graphical representation corresponding to the size of the shadowed area within the ultrasound image. This is a possibility to indicate the quality of the ultrasound image, since the size of the shadowed area with respect to the size of the ultrasound image can be considered by the operator.

In a preferred embodiment, the evaluation unit is adapted to detect a plurality of shadowed areas within the volume of interest and the display unit is adapted to display at least one sectional view of one of at least one of the shadowed areas. This is a possibility to identify separately different shadowed areas within the volume of interest and to quickly assess the relevance of the shadows.

It is preferred if the sectional views of the shadowed areas are displayed simultaneously or successively for a predefined time or on demand by the operator so that all shadowed areas can be displayed in detail. This is a possibility to increase the reliability of the medical examination since each shadowed area can be assessed in detail.

In a preferred embodiment, the two-dimensional slice is a plane within the volume of interest parallel to a direction of propagation of ultrasound waves of the ultrasound scan. This is a simple possibility to display the ultrasound image corresponding to standard ultrasound views of the region of interest so that the operator can easily determine whether relevant areas are obscured.

In a preferred embodiment, the imaging processing unit is adapted to determine image data of a plurality of different two-dimensional slices of the shadowed area, wherein the slices are disposed in a transverse direction to each other. This is a possibility to determine the three-dimensional extent of the shadowed area so that the operator can easily determine whether a region of interest is obscured.

In a preferred embodiment, the display unit is adapted to display the different sectional views of the shadowed areas. This is a possibility to display simultaneously the sectional views corresponding to the different two-dimensional slices so that the operator can easily determine whether anatomic objects are obscured by the shadowed area.

In a preferred embodiment, the positions of the different two-dimensional slices of the shadowed area are determined by an operator. This is a possibility to individually determine the two-dimensional slices within the ultrasound image.

In a preferred embodiment, the display unit is adapted to highlight the graphical representation of the shadowed area within the displayed ultrasound image. This is a simple possibility to indicate the position of the shadowed area so that the operator can easily determine whether a region of interest is obscured by the shadowed area.

In a preferred embodiment, the evaluation unit is adapted to identify anatomical objects within the volume of interest and the display unit is adapted to indicate the identified anatomical objects within the ultrasound image. This is a further possibility to increase the reliability of the ultrasound imaging, since a warning message can be displayed to inform the operator that a part of a given anatomical object is obscured. In a further preferred embodiment, the portion of the anatomical object that is obscured can also be quantified.

In a preferred embodiment, the image processing unit is adapted to determine image data of a plan view of the shadowed area corresponding to a direction of propagation of the ultrasound waves and the display unit is adapted to display the plan view image data. This is a further possibility to improve the reliability of the ultrasound imaging and the clinical examination, since the shadowed areas can be displayed in a plan view so that the operator can easily understand the geometrical location of the shadow.

In a preferred embodiment, the evaluation unit is adapted to determine a size of the shadowed area in a direction of propagation of the ultrasound waves, and wherein the display unit is adapted to display the size of the shadowed area in the plan view image data. This is a possibility to display the size of the shadowed area in the plan view image so that the operator can easily understand the spatial extend and the spatial position of the shadow. It is further preferred to display the size of the shadowed area in the plan view color-coded.

As mentioned above, since the display unit is adapted to indicate whether a shadowed area has been detected within the volume of interest or not, the operator can easily determine whether a region of interest is obscured by the shadowed area so that the reliability of the medical examination is improved. Due to the visualization of the shadowed area within the ultrasound image, the extent or the position of the shadows can help to locate the shadowed area and to distinguish whether anatomical objects or shadowed areas are visible within the ultrasound image. By means of the two-dimensional slices and the respective sectional views of the volume of interest, the operator can easily determine the position of the shadows on the basis of the standard views of the ultrasound image system. Consequently, the reliability of the ultrasound image examination is improved and the duration of the examination can be reduced.

BRIEF DESCRIPTION OF THE DRAWINGS

These and other aspects of the invention will be apparent from and elucidated with reference to the embodiment(s) described hereinafter. In the following drawings

FIGS. 2a, b show a schematic illustration of a three-dimensional raw ultrasound image and an ultrasound image including a displayed shadow;

DETAILED DESCRIPTION OF THE INVENTION

Figure 1:
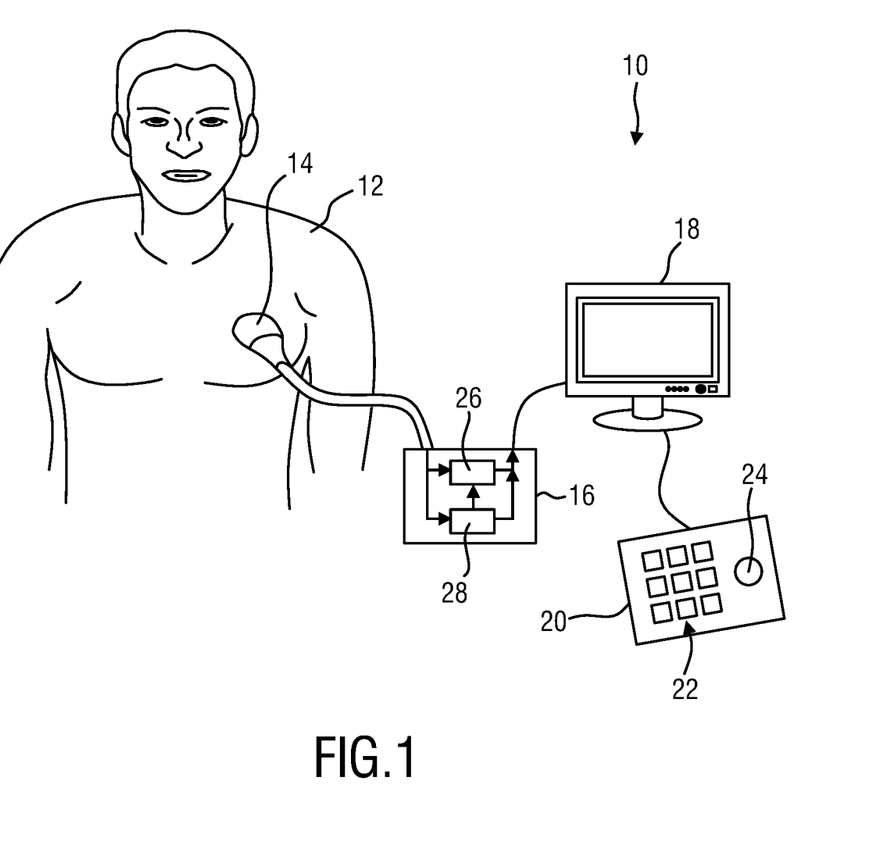
FIG. 1 shows a schematic representation of an ultrasound imaging system in use to scan a volume of a patient's body.

FIG. 1 shows a schematic illustration of an ultrasound system 10 according to an embodiment, in particular a medical three-dimensional (3D) ultrasound imaging assembly. The ultrasound imaging assembly 10 is applied to inspect a volume of interest of an anatomical side, in particular an anatomical side of a patient 12. The ultrasound imaging assembly 10 comprises an ultrasound probe 14 having at least one transducer array having a multitude of transducer elements for transmitting and/or receiving ultrasound waves. In one example, the transducer elements each can transmit ultrasound waves in form of at least one transmit impulse of a specific pulse duration, in particular a plurality of subsequent transmit pulses. The transducer elements are preferably arranged in a one-dimensional string or a two-dimensional array, in particular for providing a multiplanar or a three-dimensional image.

A 3D ultrasound scan typically involves emitting ultrasound waves that illuminate a particular volume within a body, which may be designated as volume of interest. This can be achieved by emitting ultrasound waves at multiple different angles. A set of volume data is then obtained by receiving and processing reflected waves. The set of volume data are a representation of a target volume within the patient's body.

It shall be understood that the ultrasound probe 14 may either be used in a non-invasive manner (as shown in FIG. 1) or in an invasive manner as this is usually done in TEE (not explicitly shown). The ultrasound probe 14 may be hand-held by the user of the system, for example medical staff or a doctor. The ultrasound probe 14 is applied to the body of the patient 12 so that an image of an anatomical side, in particular an anatomical object of the patient is provided.

Further, the ultrasound assembly may comprise a control unit 16 that controls the provision of an ultrasound image via the ultrasound assembly 10. The control unit 16 drives the ultrasound probe 14 and in particular the transducer elements for emitting the ultrasound waves and receives ultrasound data from the transducer elements of the ultrasound probe 14 in order to provide ultrasound images on the basis of the ultrasound data. The ultrasound assembly 10 may further comprise a display 18 for displaying the ultrasound image to the user. Still further, an input device may be provided that may comprise keys or a keyboard 22 and further inputting devices, for example a trackball 24. The input device 20 might be connected to the display 18 or directly to the control unit 16.

The control unit 16 comprises an image processing unit 26 for receiving the ultrasound data from the ultrasound probe 14 and for evaluating the ultrasound data. The image processing unit 26 provides image data corresponding to the ultrasound data received from the ultrasound probe 14. The control unit 16 further comprises an evaluation unit 28, which receives the ultrasound data from the ultrasound probe 14 and detects a shadowed area within the volume of interest as described in the following.

The evaluation unit 28 receives the ultrasound data from the ultrasound probe 14 and detects shadowed areas within the volume of interest. The shadowed areas are usually identified on the basis of a linear scan of the transducer array or a planar scan, wherein the intensity of the received ultrasound waves dependent on the detection angle of the ultrasound probe 14 is evaluated.

In a first step, a discussion is performed line by line. Suspected shadow segments are identified where the intensity of the received ultrasound waves presents a signature typical for shadows: while a first part of the signals present real anatomical information resulting in varying displayed intensities, e.g. a succession of bright or dark regions, a sudden decay is observed, followed by a long uniform very dark region.

In a second step, a 3D consolidation is performed: a shadow is detected only if a group of shadow segments with similar lengths are suspected in the same neighborhood.

If a shadowed area is detected in the ultrasound data, the evaluation unit 28 provides the information to the display unit 18 or to the image processing unit 26 so that the presence of the shadowed area can be displayed on the screen of the display unit 18. If no shadowed area is detected, this information may be also be indicated on the display screen. Alternatively, the presence of a shadowed area my be indicated on the display screen by highlighting a graphical representation of the border of the shadowed area within a three-dimensional or two-dimensional ultrasound image or by a three-dimensional representation of the shadowed area in a three-dimensional ultrasound image as described in detail in the following.

In the following, the indication of the shadowed areas is described for three-dimensional ultrasound image systems, however, the indication of the shadowed areas may also be provided for two-dimensional ultrasound image systems.

Figure 2:
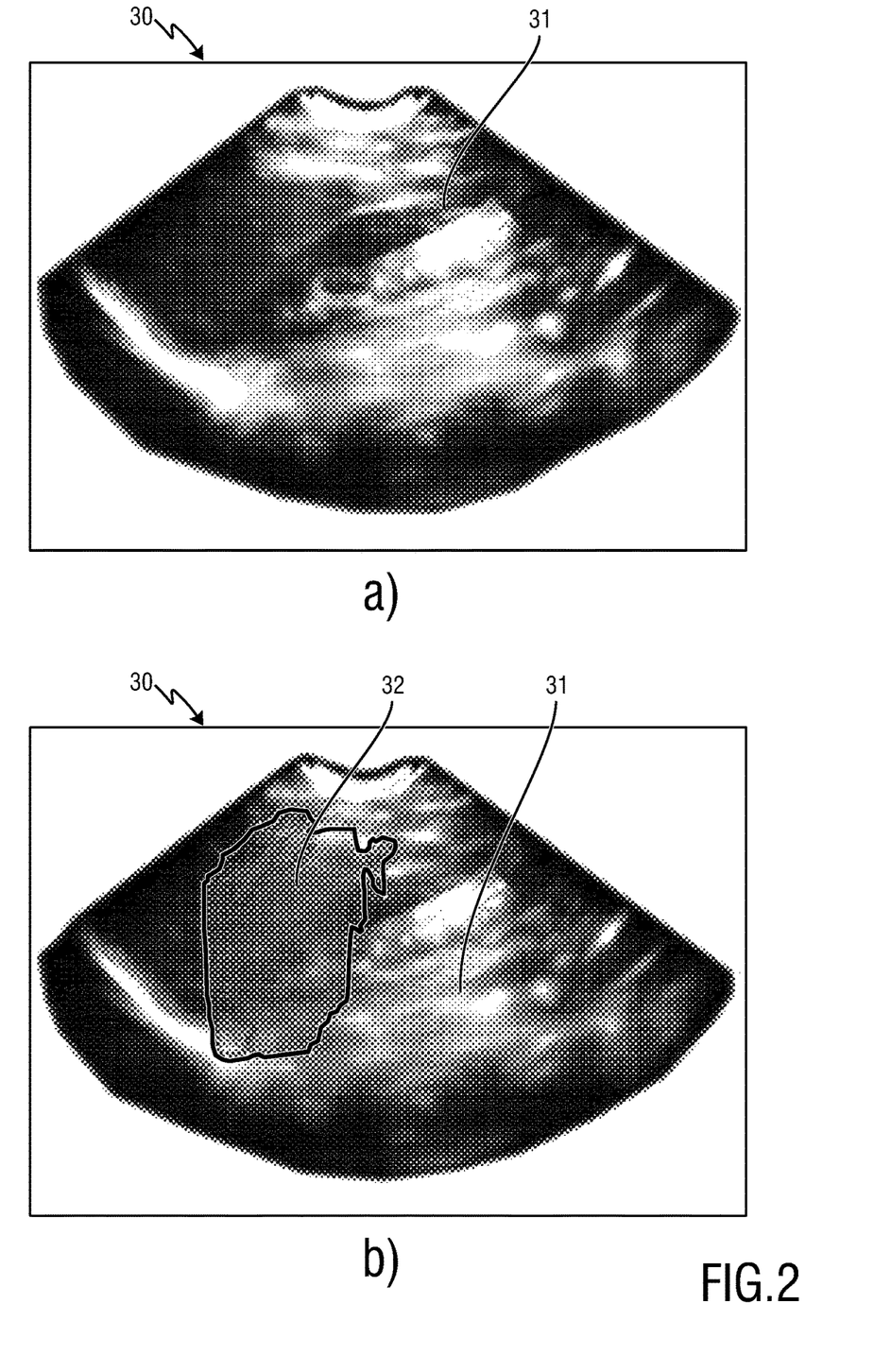

In FIG. 2a a typical three-dimensional ultrasound image is schematically shown and generally denoted by 30. The data is represented using the maximum intensity projection method (MIP). At each pixel the highest value of the volume is shown crossed by the eye of an observer that looks in the particular direction. The ultrasound data is received from a volume of interest 31 of the patient 12. Due to the multiplanar or three-dimensional illustration of the ultrasound data, shadows are difficult to identify in the three-dimensional ultrasound image 30. In FIG. 2b, the three-dimensional ultrasound image 30 is shown and a shadowed area is indicated in the image and generally denoted by 32. The shadowed area is without any indication not visible in the three-dimensional ultrasound image 30, since the different planes of the ultrasound measurements or the three-dimensional illustration of the ultrasound data hide the shadowed area 32, which may be visible more easily in a two-dimensional standard ultrasound image. The evaluation unit 28 detects the shadowed area 32 by evaluating the ultrasound data received from the ultrasound probe 14 and displays the presence of the shadowed area 32 on the display screen of the display unit 18. The indication of the shadowed area 32 may be a simple warning message displayed on the display screen so that the user can browse into the volume of interest 31 to assess whether the shadowed area 32 obscures a certain region of interest within the volume of interest 31. Additionally, the warning message may include further information on the extent and/or the position of the detected shadowed area 32.

Figure 3:
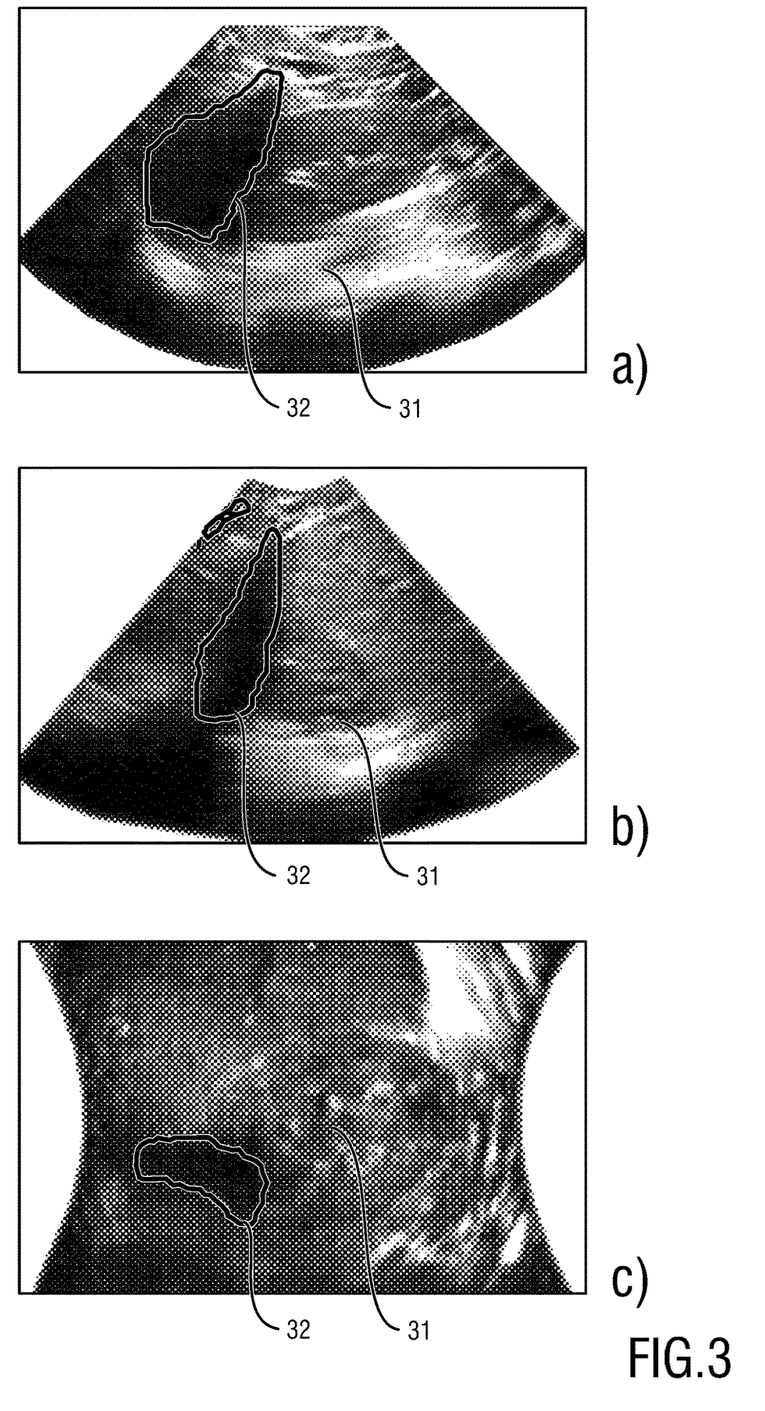
FIGS. 3a-c show schematic illustrations of two-dimensional slices of the shadow of the three-dimensional ultrasound image shown in FIG. 2a, b.

In FIG. 3a-c, a preferred embodiment of the illustration of the shadowed area 32 in different slices is schematically shown. The image processing unit 26 provides two-dimensional slices of the volume of interest 31 including the detected shadowed area 32 so that the position and the size of the shadowed area 32 can be easily identified and distinguished from anatomical objects within the volume of interest 31. The shadowed area is in this certain embodiment indicated or highlighted by illustrating the border of the shadowed area 32. The two-dimensional slices shown in FIGS. 3a and 3b are planes directed in parallel to the propagation direction of the ultrasound waves within the volume of interest 31. These two-dimensional slices show a sectional view of the volume of interest 31 corresponding to a standard two-dimensional view of an ultrasound image. The slices may be disposed in the shadowed area vertically to each other or in a different angle to each other. The slices are preferably determined automatically, however the operator may also determine the position of the slices individually e.g. by a cursor. FIG. 3a, b show that the so highlighted shadowed area 32 can be easily identified by the operator and easily distinguished from anatomical objects within the volume of interest 31. By this indication of the shadowed area 32, the operator can easily determine whether the region of interest is obscured by the shadowed area 32 and whether a different analysis or a different position of the ultrasound probe 14 may be necessary to achieve a reliable image from the region of interest. In FIG. 3c a two-dimensional plan view of the volume of interest 31 is schematically shown. The plan view is a viewing direction parallel to the propagation direction of the ultrasound waves, wherein the shadowed area 32 is highlighted by indicating the borders of the shadowed area 32.

In the case that more than one shadowed area 32 is detected, the ultrasound imaging assembly 10 may display the most relevant shadowed area 32, e.g. on the basis of the size or the position of the shadowed area 32. In that case, the user does not have to interact with the ultrasound imaging assembly by means of the input device 20 and can leave the ultrasound probe 14 in place. Alternatively, all detected shadowed areas 32 can be displayed in the two-dimensional sectional or plan views either simultaneously or successively. The shadowed areas 32 may be displayed for a couple of seconds or on demand of the operator to switch between the different shadowed areas 32. In that case also different two-dimensional slices and sectional views or plan views of the shadowed areas 32 may be displayed on the display screen of the display unit 18.

Figure 4:
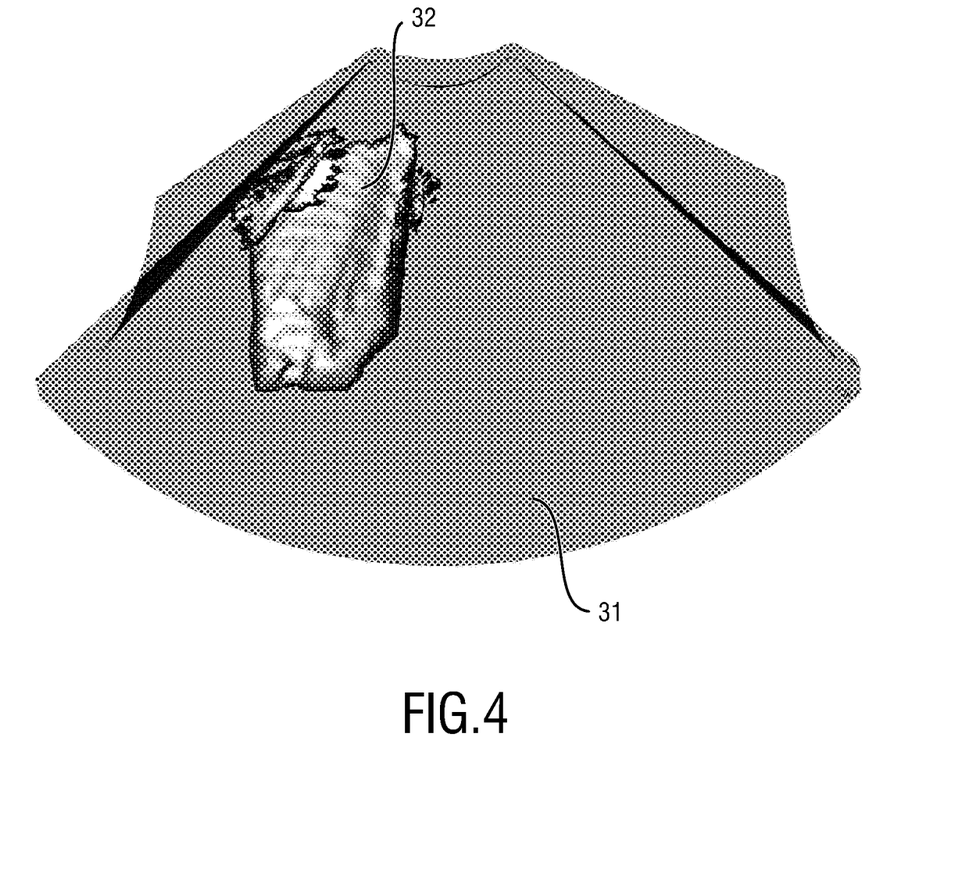
FIG. 4 shows a schematic view of a three-dimensional ultrasound image including a three-dimensional representation of a detected shadowed area.

In FIG. 4 a three-dimensional representation of the ultrasound data is schematically shown. The volume of interest 31 is displayed as a cone, wherein the shadowed area 32 is displayed as a three-dimensional representation within the volume of interest 31. The three-dimensional representation shown in FIG. 4 is a virtual three-dimensional image displayed on a two-dimensional display screen, wherein a three-dimensional illustration can be achieved by rotating the respective image. In the three-dimensional representation shown in FIG. 4, further reference objects or anatomic objects may be highlighted in order to help the understanding of the three-dimensional volume of interest 31 and to understand which part of the volume of interest is obstructed by the shadowed area 32. It provides also a clear representation for the clinician to immediately understand where the suspected region lies geographically. He can then navigate efficiently to the interesting slices. Alternatively, a tool can be provided that displays automatically the corresponding slices when he clicks over the representation shown in FIG. 4. The anatomic objects may be organs or bones within the patient's body 12. A warning message can be provided if one anatomical object is obscured or partially obscured. The portion of the anatomical object that is obscured can be quantified and the amount of the obscured portion can be displayed on the display screen e.g. 30% of the kidney is obscured by a shadow. The warning message may be provided if a certain amount of an anatomic object is obscured such as a threshold level, e.g. if more than 20% of the kidney is obscured by a shadow.

Figure 5:
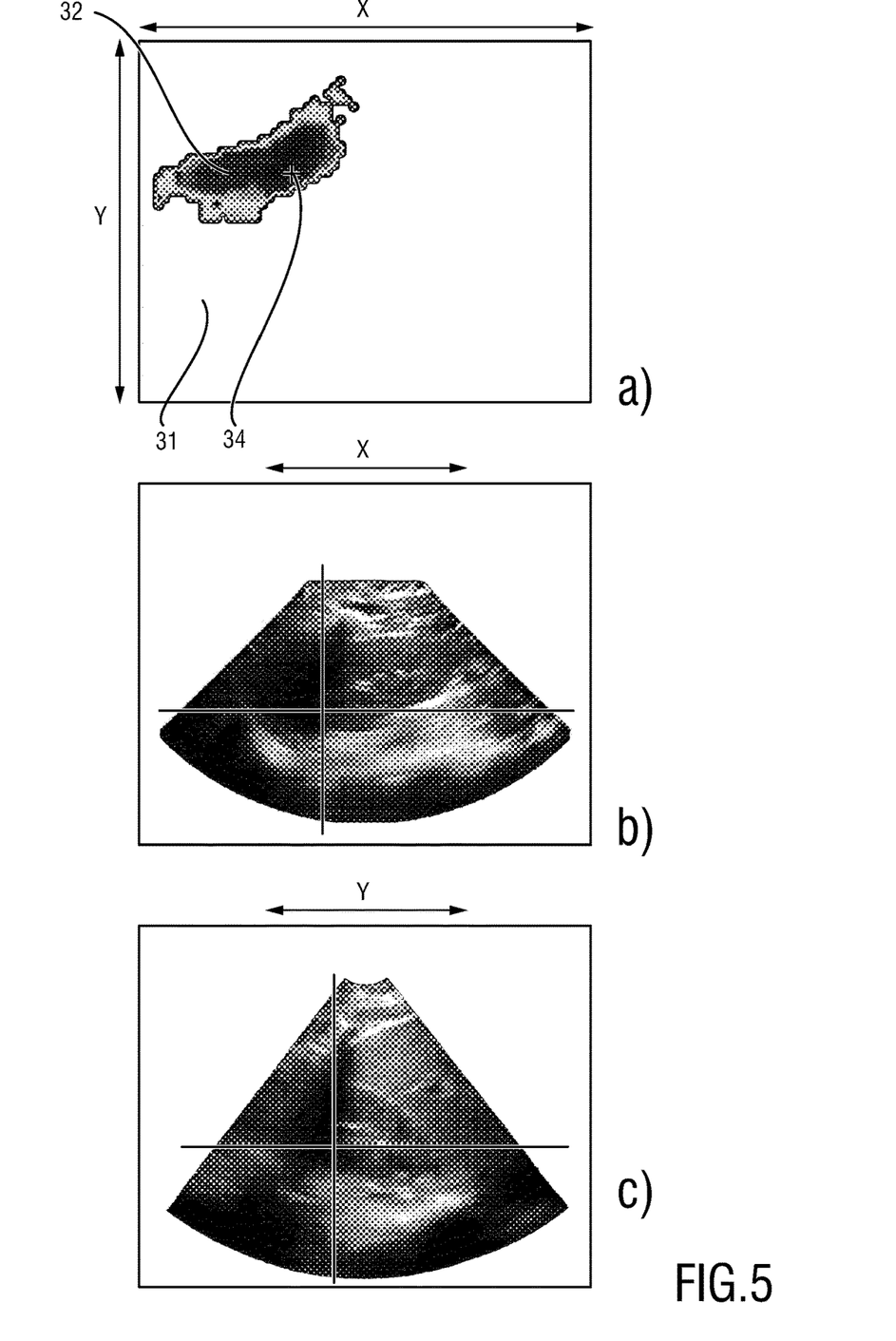
FIGS. 5a-c show a graphical representation of the shadowed area and two sectional views corresponding to a selected position of the shadowed area.

In FIG. 5 a further embodiment of displaying the shadowed area 32 is schematically shown. The shadowed area is displayed in a plan view corresponding to a viewing direction parallel to the propagation direction of the ultrasound waves. The plan view is shown in FIG. 5a, wherein the shadowed area 32 may be displayed or highlighted color-coded so that the shadowed area 32 can be easily identified. The color code of the plan view image shown in FIG. 5a represents the depth or the length of the shadowed area. The depth or the length of the shadowed area in the direction of the propagation of the ultrasound waves is measured or detected and indicated in the color-coded image. The non-shadowed area is not-colored e.g. black or white.

In order to analyze the depth of the shadowed area 32, two-dimensional slices through the shadowed area 32 can be provided additionally as a sectional view corresponding to a standard view of ultrasound images which are schematically shown in FIGS. 5b and 5c. The position of the slices may be determined automatically by means of the ultrasound imaging assembly or may be selected by the operator by means of the cursor 34.

The two-dimensional slices shown in FIGS. 5b and c are planes within the volume of interest 31 which are disposed orthogonal to each other or in different angles e.g. 30°. The two-dimensional slice shown in FIG. 5b corresponds to the x direction and the slice shown in FIG. 5c corresponds to the y direction of the plan view shown in FIG. 5a. By means of these different two-dimensional slices and the corresponding sectional views, the depth of the shadowed area 32 can be easily visualized, wherein the size and the depth do not need to be certainly displayed in the sectional views shown in FIGS. 5b and c.

The synthetic representation shown in FIGS. 4 and 5 may be combined with the visualization of the slices shown in FIGS. 3a, b. The displaying of the shadowed areas 32 may be provided in real time during the ultrasound examination process so that the operator may move the ultrasound probe 14 to a different position so that the shadowed area 32 is moved to a different position, so that the respective area of interest is not obscured. Further, other artifacts which obscure certain areas within the ultrasound image may be detected and displayed, e.g. dirty shadowing, comet tails or the like.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An ultrasound imaging assembly, comprising:
an image processing unit adapted to receive and evaluate at least one set of ultrasound data resulting from an ultrasound scan of a volume of interest and to provide corresponding image data on the basis of the at least one set of ultrasound data, a display unit adapted to display an ultrasound image on the basis of the image data, an evaluation unit adapted to:
  detect, based on the ultrasound data, a shadowed portion of the volume of interest, wherein the shadowed portion is associated with a boundary between two tissues of different impedance; and
  determine a three-dimensional boundary of the shadowed portion within the volume of interest based on lengths of the shadowed portion along respective directions of propagation of ultrasound waves of the ultrasound scan, wherein the image processing unit is further adapted to determine ultrasound image data of a plurality of different two-dimensional slices of the shadowed portion, wherein the plurality of different two-dimensional slices are disposed in a transverse direction to each other, and wherein the display unit is adapted to display a graphical representation of a cross-section of the three-dimensional boundary of the shadowed portion superimposed on at least one two-dimensional image slice of the plurality of different two-dimensional slices.

2. The ultrasound imaging assembly as claimed in claim 1, wherein the display unit is adapted to display a graphical representation corresponding to at least one of the lengths of the shadowed portion superimposed on the ultrasound image.

3. The ultrasound imaging assembly as claimed in claim 1, wherein the evaluation unit is adapted to detect a plurality of shadowed portions within the volume of interest and wherein the display unit is further adapted to display sectional views of the plurality of the shadowed portions.

4. The ultrasound imaging assembly as claimed in claim 1, wherein positions of the plurality of different two-dimensional slices of the shadowed portion are determined by an operator.

5. The ultrasound imaging assembly as claimed in claim 1, wherein the display is adapted to highlight the graphical representation of the cross-section of the three-dimensional boundary of the shadowed portion superimposed on the displayed at least one two-dimensional image slice of the plurality of different two-dimensional slices.

6. The ultrasound imaging assembly as claimed in claim 1, wherein the image processing unit is further adapted to determine image data of a plan view of the shadowed portion corresponding to one of the directions of propagation of the ultrasound waves and wherein the display unit is adapted to display the plan view image data.

7. The ultrasound imaging assembly as claimed in claim 6, wherein the display unit is adapted to display at least one of the lengths of the shadowed portion in the plan view image data.

8. The ultrasound imaging assembly as claimed in claim 1, wherein the evaluation unit is configured to detect the shadowed portion based on determining that for at least two adjacent scan lines:
  a first part of the scan lines include a succession of bright or dark regions, and
  a second part of the scan lines include a uniform dark region.

9. The ultrasound imaging assembly as claimed in claim 1, wherein the plurality of different two-dimensional slices are disposed parallel to one of the directions of propagation of ultrasound waves of the ultrasound scan.

10. The ultrasound imaging assembly as claimed in claim 1, wherein the display unit is adapted to display the plurality of different two-dimensional slices simultaneously, wherein each of the displayed plurality of different two-dimensional slices includes a graphical representation of a corresponding cross-section of the three-dimensional boundary of the shadowed portion superimposed thereon.

11. A method for displaying ultrasound images, the method comprising the steps of:
  receiving at least one set of ultrasound data resulting from an ultrasound scan of a volume of interest,
  evaluating the at least one set of ultrasound data,
  providing corresponding image data on the basis of the at least one set of ultrasound data,
  displaying an ultrasound image on a display unit on the basis of the image data,
  detecting, based on the ultrasound data, whether a shadowed portion associated with a boundary between two tissues of different impedance is present,
  determining a three-dimensional boundary of the shadowed portion within the volume of interest based on lengths of the shadowed portion along respective directions of propagation of ultrasound waves of the ultrasound scan,
  determining ultrasound image data of a plurality of different two-dimensional slices of the shadowed portion, wherein the plurality of different two-dimensional slices are disposed in a transverse direction to each other, and
  displaying a graphical representation of a cross-section of the three-dimensional boundary of the shadowed portion superimposed on at least one two-dimensional image slice of the plurality of different two-dimensional slices on the display unit.

12. An ultrasound transducer assembly, comprising an ultrasound transducer unit including a plurality of ultrasound transducer elements for transmitting and receiving ultrasound waves and an ultrasound imaging assembly as claimed in claim 1 for evaluating and displaying ultrasound data received from the ultrasound transducer unit.

13. The method as claimed in claim 11, comprising:
  displaying a graphical representation corresponding to at least one of the lengths of the shadowed portion superimposed on the ultrasound image.

14. The method as claimed in claim 11, comprising:
  detecting a plurality of shadowed portions within the volume of interest, and
  displaying sectional views of the plurality of the shadowed portions.

15. The method as claimed in claim 11, comprising in response to an operator, determining positions of the plurality of different two-dimensional slices of the shadowed portion.

16. The method as claimed in claim 11, comprising determining image data of a plan view of the shadowed portion corresponding to one of the directions of propagation of the ultrasound waves and displaying the plan view image data.

17. The method as claimed in claim 16, comprising displaying at least one of the lengths of the shadowed portion in the plan view image data.

18. The method as claimed in claim 11, comprising highlighting the graphical representation of the cross-section of the boundary of the shadowed portion superimposed on the displayed at least one two-dimensional image slice of the plurality of different two-dimensional slices.

* * * * *